United States Patent [19]
Florio et al.

[11] Patent Number: 5,601,613
[45] Date of Patent: Feb. 11, 1997

[54] METHOD AND APPARATUS FOR PROVIDING ENHANCED 2:1 BLOCK RESPONSE WITH RATE-RESPONSIVE AV DELAY IN A PACEMAKER

[75] Inventors: Joseph J. Florio, Sunland; Roy B. Medlin, West Hills, both of Calif.

[73] Assignee: Pacesetter, INc., Sylmar, Calif.

[21] Appl. No.: 385,023

[22] Filed: Feb. 7, 1995

[51] Int. Cl.$^6$ .................................................. A61N 1/362
[52] U.S. Cl. ............................................................ 607/14
[58] Field of Search ................................... 607/9, 14, 15

[56] References Cited

U.S. PATENT DOCUMENTS 4,429,697  2/1984  Nappholz et al. ........................ 607/9
5,103,820  4/1992  Markowitz ................................ 607/9
5,395,397  3/1995  Lindgren et al. ......................... 607/14

*Primary Examiner*—William E. Kamm

[57] ABSTRACT

An implantable dual-chamber pacemaker programmed to operate primarily in an atrial tracking mode is provided, where the pacemaker maintains a consistent atrial rate of entry into, and exit from, a 2:1 block response mode by setting rate-responsive AV delay values in accordance with a continually monitored intrinsic atrial rate incorporating atrial events occurring during atrial refractory periods. The atrial rate of entry into, and exit from the 2:1 block response mode is determined by the length of a total atrial refractory period, which is the sum of the rate-responsive AV delay and a programmable refractory period.

18 Claims, 3 Drawing Sheets

| "FUNCTIONAL" ATRIAL RATE | RATE RESPONSIVE AV DELAY VALUES | TOTAL ATRIAL REFRACTORY PERIOD (TARP) FOR PVARP=275ms |
|---|---|---|
| ATRIAL RATE <= TR1 | AVD_MAX: 200ms | TARP_MAX: 475ms |
| TR1 ATRIAL RATE < TR2 | AVD_1: 150ms | TARP_1: 425ms |
| ATRIAL RATE => TR2 | AVD_MAX: 100ms | TARP_MIN: 375ms |

METHOD AND APPARATUS FOR PROVIDING ENHANCED 2:1 BLOCK RESPONSE WITH RATE-RESPONSIVE AV DELAY IN A PACEMAKER

FIELD OF THE INVENTION

The present invention relates generally to cardiac pacemakers, and more particularly, to a rate-responsive, programmable, dual-chamber pacemaker programmed to operate in an atrial tracking mode, where the pacemaker maintains a consistent atrial rate of entry into, and exit from, a 2:1 block response mode by setting rate-responsive AV delay values in accordance with an intrinsic atrial rate continually sensed during atrial refractory periods.

BACKGROUND OF THE INVENTION

Essentially, the heart is a pump which pumps blood throughout the body. It consists of four chambers—two atria and two ventricles. In order for the heart to efficiently perform its function as a pump, the atrial muscles and ventricular muscles should contract in a proper sequence and in a timed relationship.

In a given cardiac cycle (corresponding to one "beat" of the heart), the two atria contract, forcing the blood therein into the ventricles. A short time later, the two ventricles contract, forcing the blood therein to the lungs (from the right ventricle) or through the body (from the left ventricle). Meanwhile, blood from the body fills the right atrium and blood from the lungs fills the left atrium, waiting for the next cycle to begin. A typical healthy adult heart may beat at a rate of 60–80 beats per minute (bpm) while at rest, and may increase its rate to 140–180 bpm when the adult is engaging in strenuous physical exercise, or undergoing other physiologic stress.

The healthy heart controls its rhythm from its SA node, located in the upper portion of the right atrium. The SA node generates an electrical impulse at a rate commonly referred to as the "sinus" or "intrinsic" rate. This impulse is delivered to the atrial tissue when the atria are to contract and, after a suitable delay (on the order of 140–220 milliseconds), propagates to the ventricular tissue when the ventricles are to contract.

When the atria contract, a detectable electrical signal referred to as a P-wave is generated. When the ventricles contract, a detectable electrical signal referred to as an R-wave is generated. The R-wave is much larger than the P-wave, principally because the ventricular muscle tissue is much more massive than the atrial muscle tissue. The atrial muscle tissue need only produce a contraction sufficient to move the blood a very short distance—from the respective atrium to its corresponding ventricle. The ventricular muscle tissue, on the other hand, must produce a contraction sufficient to push the blood over a long distance (e.g., through the complete circulatory system of the entire body).

Other electrical signals or waves are also detectable within a cardiac cycle, such as a Q-wave (which is the negative deflection immediately preceding an R-wave), an S-wave (which is the negative deflection immediately following an R-wave), and a T-wave (which represents the repolarization of the ventricular muscle tissue).

It is the function of a pacemaker to provide electrical stimulation pulses to the appropriate chamber(s) of the heart (atrium, ventricle, or both) in the event the heart is unable to beat on its own (i.e., in the event either the SA node fails to generate its own natural stimulation pulses at an appropriate sinus rate, or in the event such natural stimulation pulses do not effectively propagate to the appropriate cardiac tissue). Most modern pacemakers accomplish this function by operating in a "demand" mode where stimulation pulses from the pacemaker are provided to the heart only when it is not beating on its own, as sensed by monitoring the appropriate chamber of the heart for the occurrence of a P-wave or an R-wave. If a P-wave or an R-wave is not sensed within a prescribed period of time (which period of time is often referred to as the "escape interval"), then a stimulation pulse is generated at the conclusion of this prescribed period of time and delivered to the appropriate heart chamber via a pacemaker lead.

Modern programmable pacemakers are generally of two types: (1) single-chamber pacemakers, and (2) dual-chamber pacemakers. In a single-chamber pacemaker, the pacemaker provides stimulation pulses to, and senses cardiac activity within, a single-chamber of the heart (e.g., either the right ventricle or the right atrium). In a dual-chamber pacemaker, the pacemaker provides stimulation pulses to, and senses cardiac activity within, two chambers of the heart (e.g., both the right atrium and the right ventricle). The left atrium and left ventricle can also be paced, provided that suitable electrical contacts are made therewith.

Much has been written and described about the various types of pacemakers and the advantages and disadvantages of each. For example, commonly-assigned U.S. Pat. No. 4,712,555 of Thornander et al. presents background information about pacemakers and the manner in which they interface with a patient's heart. This patent is hereby incorporated by reference in its entirety.

One of the most versatile programmable pacemakers available today is the DDDR pacemaker. This pacemaker represents a fully automatic pacemaker which is capable of sensing and pacing in both the atrium and the ventricle, and is also capable of adjusting the pacing rate based on one or more physiological factors, such as the patient's activity level. When functioning properly, the DDDR pacemaker can limit certain drawbacks associated with the use of pacemakers. For example, the DDDR pacemaker can maintain AV synchrony while providing bradycardia support.

In general, DDDR pacing has four functional states: (1) P-wave sensing, ventricular pacing (PV); (2) atrial pacing, ventricular pacing (AV); (3) P-wave sensing, R-wave sensing (PR); and (4) atrial pacing, R-wave sensing (AR). Advantageously, for the patient with complete or partial heart block, the PV state of the DDDR pacemaker tracks the atrial rate which is set by the heart's SA node, and then paces in the ventricle at a rate that follows this atrial rate. Because the rate set by the SA node represents the rate at which the heart should beat in order to meet the physiologic demands of the body (at least for a heart having a properly functioning SA node) the rate maintained in the ventricle by such a pacemaker is truly physiologic.

Those skilled in the art have long recognized the advantages of using an atrial tracking pacemaker. For example, U.S. Pat. No. 4,624,260 to Baker, Jr. et al. discloses a microprocessor-controlled dual-chamber pacemaker having conditional atrial tracking capability. Similarly, U.S. Pat. No. 4,485,818 of Leckrone et al. discloses a microprocessor-based pacemaker which may be programmed to operate in one of a plurality of possible operating modes, including an atrial rate tracking mode.

Unfortunately, in some instances, a given patient may develop fast atrial rhythms which result from a pathologic arrhythmia such as a pathological tachycardia, fibrillation or flutter. In these cases, a DDDR pacemaker may pace the ventricle in response to the sensed atrial arrhythmia up to a programmed maximum tracking rate (MTR). The MTR defines the upper limit for the ventricular rate when the pacemaker is tracking the intrinsic atrial rate. As a result, the MTR sets the limit above which the ventricles cannot be paced, regardless of the intrinsic atrial rate. Thus, the purpose of the MTR is to prevent rapid ventricular stimulation, which could occur if the intrinsic atrial rate becomes very high and the pacemaker attempts to track atrial activity with 1:1 AV synchrony.

When the intrinsic atrial rate exceeds the MTR the pacemaker may initiate one or more upper atrial rate response functions—such as automatically switching the pacemaker's mode of operation from an atrial tracking mode to a non-atrial rate tracking mode. However, in some cases mode-switching may not be a desirable upper rate response. Most previously known mode-switching techniques are based in whole or in part on the patient's sensed atrial rate exceeding a certain threshold atrial rate (such as the MTR). This mode-switching criterion may cause problems for patients who exhibit normal sinus tachycardia due to physical activity. Another difficulty associated with mode-switching techniques is that mode-switching occasionally occurs due to electrical noise present in the atrial sensing channel of the pacemaker, or due to a one-of-a-kind fast P-wave. In these instances, rates slightly exceeding the MTR are not indicative of a pathologic arrhythmia. These patients may thus be subjected to undesirably frequent mode-switching occurrences as their atrial rates exceed and then drop below the MTR.

The heart's natural response to a high atrial rate involves a phenomenon known as "blocking"—where the AV node attempts to maintain a form of AV synchrony by "dropping out" occasional ventricular beats when the high atrial rate exceeds a certain natural threshold i.e., the refractory period of the heart tissue. The blocking phenomenon is often expressed as a ratio of the atrial beats to the ventricular beats (e.g. 6:5, 4:3, etc.). Of particular importance is a 2:1 block condition where there are two atrial beats for every one ventricular beat. The 2:1 block condition is a natural response to a very high atrial rate, during which full ventricular rate synchronization (i.e. at a 1:1 ratio) would be dangerous to the patient.

Implantable stimulation devices emulate this 2:1 condition, by tracking P-waves up to the device's programmed total refractory period (TARP) of the heart. That is, P-waves which fall in the total refractory period are not tracked, and the device is said to have a "2:1 response mode".

In addition, a 2:1 block response mode decreases the likelihood of a pacemaker mediated tachycardia. Pacemaker mediated tachycardia may occur when pacing pulses delivered in the ventricle causes a retrograde P-wave to be conducted to the atria immediately after each pacing pulse is delivered. This forces the apparent atrial rate to increase due to the additional P-waves occurring during a cardiac cycle during which a ventricular pulse was delivered. Since the ventricle is typically paced in full synchrony with the atrial rate, a tachycardia develops as the ventricular pacing rate increases to follow the high atrial rate caused by the retrograde conduction. During the 2:1 block response mode, the ventricles are paced at a lower rate than the atrial rate, because P-waves occurring soon after ventricular events are ignored for the purposes of calculating the ventricular pacing rate. As a result, the 2:1 block response mode prevents the pacemaker from pacing the ventricles at a tachycardia rate.

The 2:1 block response mode is an effective response for dealing with short incidences of high atrial rates and in preventing occurrence of a pacemaker mediated tachycardia resulting from retrograde P-waves. However, the 2:1 block response mode may become uncomfortable for the patient if it is maintained for an extended period of time due to programmed long atrial refractory periods, because the pacing rate will be ½ the required physiologic rate.

Some dual-chamber pacemakers have attempted to emulate the natural block condition as an upper atrial rate response by reducing the ventricular pacing rate when the intrinsic atrial rate exceeds the MTR. Since the MTR is programmed by the medical practitioner as the maximum safe rate at which the ventricles may be paced, when the intrinsic atrial rate exceeds the MTR a dangerous upper rate condition is deemed to exist and the ventricular pacing rate is reduced in order to prevent it from exceeding the MTR.

Pacemakers incorporate a programmable parameter known as an atrial refractory period, which is initiated by either a paced or sensed cardiac event. The atrial refractory period, also called a total atrial refractory period (TARP), is made up of two segments. The first segment, known as the AV Delay (AVD), is initiated by a paced or sensed atrial event. The second segment, known as the post ventricular atrial refractory period (PVARP), is initiated by a paced or sensed ventricular event. The TARP (measured in milliseconds (ms)) is inversely proportional to the rate at which 2:1 block occurs, that is, the 2:1 block rate occurs is 60,000÷TARP for conversion to beats per minute (bpm). As a result, when the intrinsic atrial rate exceeds the rate specified by the TARP, one or more atrial events occur during the TARP. For example, if the 2:1 block rate is 160 bpm, then the TARP is 60,000÷160, or 375 ms. If the intrinsic atrial rate is 200 bpm, the interval between the atrial events is 60,000÷200, or 300 ms, which means that one atrial event occurs within the TARP of 375 ms. Therefore, atrial events occurring during the TARP are not counted by the pacemaker for the purpose of pacing the ventricles. Instead, only atrial events occurring outside the TARP are counted in order to derive a "sensed functional atrial rate". The pacemaker then paces the ventricles at a rate that follows the sensed functional atrial rate. As the intrinsic atrial rate increases, the occurrence of an atrial event during the TARP becomes more probable, until every other atrial event falls into the TARP. Since the atrial events occurring during the TARP are not counted, the sensed functional atrial rate (and thus the ventricular pacing rate) is approximately one half of the intrinsic atrial rate and a 2:1 block response mode is entered. When the intrinsic atrial rate begins to decrease, a decreasing number of atrial events occur within the TARP. When the intrinsic atrial rate falls below the 2:1 block rate, it is equal to the sensed functional atrial rate, since no atrial events occur during the TARP (i.e., no atrial events are skipped).

Advancements in pacemaker technology have been driven by a desire to approximate true physiological cardiac activity through pacing. One pacemaker function that mimics physiological behavior of the heart is rate-responsive AV delay (RRAVD). The RRAVD allows the pacemaker to respond to changes in the intrinsic atrial rate by progressively decreasing the AVD in preprogrammed increments from its base value as the intrinsic atrial rate increases until a minimum preset shortened AVD value is reached. This function is referred to as "rate-responsive AV delay shortening". This minimum preset AVD is usually reached when the intrinsic atrial rate exceeds an upper rate threshold but before the 2:1 block condition is entered. Thus, the RRAVD combined with the PVARP enables the TARP to change in response to changes in the atrial rate. A rate-responsive refractory period is advantageous because it closely emulates the physiological behavior of the heart and increases patient comfort.

Similar to most rate-responsive pacemaker functions, the RRAVD of previously known pacemakers is based on the sensed functional atrial rate since previously known rate-responsive pacemakers equipped with the RRAVD function do not sense atrial events occurring during the TARP. This does not pose a problem when the intrinsic atrial rate is below the 2:1 block rate since up to that point, the intrinsic atrial rate is equal to the sensed functional atrial rate. However, when the intrinsic atrial rate exceeds the 2:1 block rate, the sensed functional atrial rate begins to drop in value as atrial events falling into the TARP are ignored. When the 2:1 block response mode is reached at a block entry rate, which is typically equal to the TARP, the RRAVD is reset from its minimum value to its base value, because according to the sensed functional atrial rate, the atrial rate is far below the upper rate limit. This phenomenon results in an adjustment of the TARP to a higher value and thus changes a block exit rate at which the 2:1 block condition may be exited. As a result, the block exit rate is lower than the block entry rate, because the block exit rate is based on the higher TARP (incorporating the maximum value AVD), while the block entry rate is based on a lower TARP (incorporating the minimum AVD). Thus, a patient will be forced to remain in the 2:1 block response mode longer than necessary, because in order for the pacemaker to exit from the 2:1 block response mode, the intrinsic atrial rate must drop below the block exit rate, a lower rate than the block entry rate at which the 2:1 block response mode was entered.

Inconsistent rates of entry into and exit from 2:1 block are contradictory to the physiological behavior of the heart (where the rates of entry into and exit from naturally occurring 2:1 block condition are relatively consistent), and may cause discomfort to the patient. Furthermore, inconsistent rates of entry into and exit from 2:1 block force the pacemaker to maintain the 2:1 block response mode longer than is necessary further increasing the likelihood of discomfort associated with an extended 2:1 block response mode.

Thus, it would be desirable for a pacemaker equipped with a RRAVD function to maintain consistent rates of entry into and exit from a 2:1 block response mode.

SUMMARY OF THE INVENTION

The disadvantages and limitations discussed above are overcome by the present invention. In accordance with this invention, an implantable dual-chamber pacemaker programmed to operate primarily in an atrial tracking mode is provided, where the pacemaker maintains a consistent atrial rate of entry into, and exit from, a 2:1 block response mode by setting rate-responsive AV delay values in accordance with a continually monitored intrinsic atrial rate incorporating atrial events occurring during atrial refractory periods.

The pacemaker of the present invention includes a control system for controlling the operation of the pacemaker, a set of leads for receiving atrial and ventricular signals and for delivering atrial and ventricular stimulation pulses, a set of amplifiers for amplifying the atrial and ventricular signals, and pulse generators for generating atrial and ventricular stimulation pulses. In addition, the pacemaker includes memory for storing operational parameters for the control system and for storing data acquired by the control system for later retrieval by the medical practitioner using an external programmer. The pacemaker also includes a telemetry circuit for communicating with the external programmer.

The pacemaker of the present invention is provided with a rate-responsive AV delay (RRAVD) which changes its value in response to changes in the intrinsic atrial rate. When the intrinsic atrial rate is lower than or equal to a first threshold rate (TR1), the RRAVD is set to its highest value. When the intrinsic atrial rate is between the TR1 and a second threshold rate (TR2), the RRAVD is set to one or more intermediate values. Finally, when the intrinsic atrial rate equals or exceeds TR2, the RRAVD is set to its minimum value. The intrinsic atrial rate-based RRAVD is advantageous because it mimics the natural shortening of the refractory periods when the atrial rate increases.

Unlike previously known rate-responsive pacemakers which do not sense the atrial events occurring during refractory periods (thus, ignoring the intrinsic atrial rate when it exceeds the TARP), and which base the RRAVD settings on the sensed functional atrial rate, the pacemaker of the present invention continually monitors the intrinsic atrial rate by sensing all atrial events, even those falling into the refractory periods, and bases the RRAVD on the intrinsic atrial rate. When the intrinsic atrial rate exceeds the TR2, the RRAVD is set to its minimum value, thus causing the TARP to be set to its minimum value as well. This minimum TARP is inversely proportional to the block entry rate since the block entry rate equals 60,000 divided by the TARP.

When the intrinsic atrial rate exceeds the block entry rate, the pacemaker continues to monitor the intrinsic atrial rate value and the RRAVD remains at its minimum value since the intrinsic atrial rate is higher than the block entry rate. As a result, the TARP remains at a relatively constant value during the 2:1 block response mode (i.e., while the intrinsic atrial rate is greater than the block entry rate). Because the TARP remains relatively constant during the 2:1 block response mode, the block exit rate is based on the same TARP as is the block entry rate. As a result, the block exit rate is consistent with the block entry rate. The sensed functional atrial rate is used for determining the ventricular pacing rate and not for setting the RRAVD.

The pacemaker of the present invention closely mimics the physiological behavior of a healthy heart and improves the comfort of a patient by sensing all atrial events, even those falling into the refractory periods, and by basing the RRAVD settings on the intrinsic atrial rate in order to provide consistent rates of entry into and exit from a 2:1 block response mode. In another aspect of this invention, a method for providing consistent rates of entry into, and exit from, a 2:1 block response mode is provided.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which:

FIG. 5 is a logic flow diagram representing an enhanced 2:1 block response control program executed by the control system of the pacemaker shown in FIG. 1, for providing consistent rates of entry into, and exit from, a 2:1 block response mode in accordance with the principles of the present invention.

DETAILED DESCRIPTION OF THE PREFERRED EMBODIMENT

Figure 1:
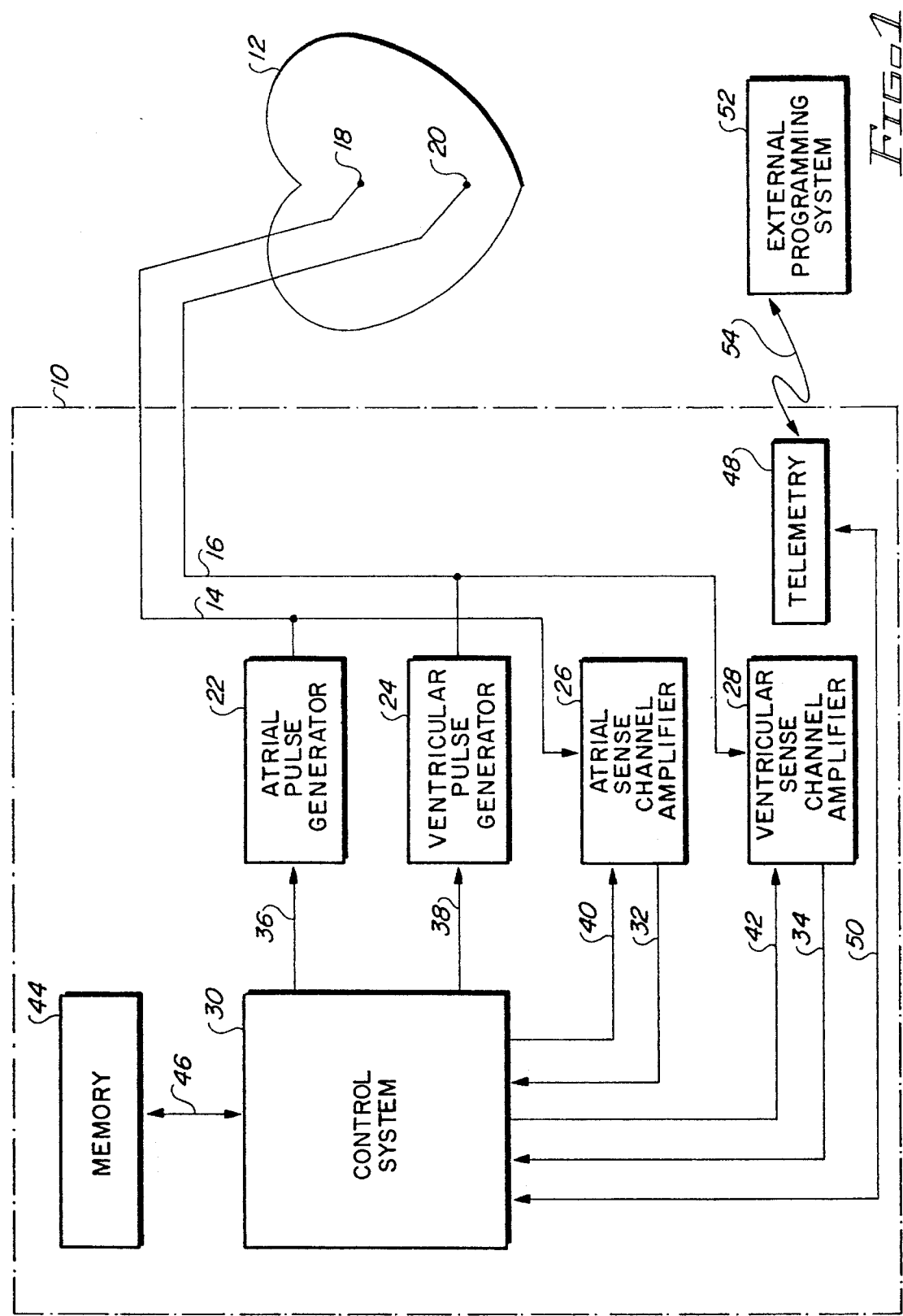
FIG. 1 is a block diagram of a dual-chamber pacemaker in accordance with the principles of the present invention.

A pacemaker 10 in accordance with this invention is shown in FIG. 1. The pacemaker 10 is coupled to a heart 12 by way of leads 14 and 16, the lead 14 having an electrode 18 which is in contact with one of the atria of the heart 12, and the lead 16 having an electrode 20 which is in contact with one of the ventricles. The lead 14 carries stimulating pulses to the electrode 18 from an atrial pulse generator 22, while the lead 16 carries stimulating pulses to the electrode 20 from a ventricular pulse generator 24. In addition, electrical signals from the atria are carried from the electrode 18, through the lead 14 to the input terminal of an atrial sense amplifier 26. Electrical signals from the ventricles are carried from the electrode 20, through the lead 16 to the input terminal of a ventricular sense amplifier 28.

Controlling the dual-chamber pacemaker 10 is a control system 30. The control system 30 is preferably a microprocessor-based system such as the one disclosed in commonly-assigned U.S. Pat. No. 4,940,052 of Mann, which is hereby incorporated by reference in its entirety. The control system 30 may also be a state logic-based system such as the one disclosed in commonly-assigned U.S. Pat. No. 4,944,298 of Sholder, which is hereby incorporated by reference in its entirety. The control system 30 also includes a real-time clock (not shown) for providing timing for monitoring cardiac events and for timing the application of therapeutic pulses by the pulse generators 22 and 24.

The control system 30 receives the output signals from the atrial amplifier 26 over a signal line 32. Similarly, the control system 30 receives the output signals from the ventricular amplifier 28 over a signal line 34. These output signals are generated each time that an atrial event (e.g., a P-wave) or a ventricular event (e.g., an R-wave) is sensed within the heart 12.

The control system 30 also generates an atrial trigger signal which is sent to the atrial pulse generator 22 over a signal line 36, and a ventricular trigger signal which is sent to the ventricular pulse generator 24 over a signal line 38. These trigger signals are generated each time that a stimulation pulse is to be generated by one of the pulse generators 22 or 24. The atrial stimulation pulse is referred to simply as the "A-pulse," and the ventricular stimulation pulse is referred to as the "V-pulse."

During the time that either an A-pulse or a V-pulse is being delivered to the heart 12, the corresponding atrial amplifier 26 or the ventricular amplifier 28 is typically disabled by way of a blanking signal presented to the appropriate amplifier from the control system 30 over a signal line 40 for the atrial amplifier 26 or a signal line 42 for the ventricular amplifier 28. This blanking action prevents the amplifiers 26 and 28 from becoming saturated with the relatively large stimulation pulses which are present at their input terminals during pacing pulse delivery. This blanking action also prevents residual electrical signals (known as "afterpotentials") present in the muscle tissue as a result of the pacemaker stimulation from being interpreted as atrial or ventricular events.

The pacemaker 10 also includes a memory circuit 44 which is coupled to the control system 30 through a suitable data bus 46. The memory circuit 44 allows certain control parameters used by the control system 30 in controlling the operation of the pacemaker 10 to be programmably stored and modified, as required, in order to customize the operation of the pacemaker 10 to suit the needs of a particular patient. In addition, data sensed during the operation of the pacemaker 10 may be stored in the memory circuit 44 for later retrieval and analysis.

A telemetry circuit 48 is further included in the pacemaker 10. The telemetry circuit 48 is connected to the control system 30 by way of a suitable command/data bus 50. In turn, the telemetry circuit 48 may be selectively coupled to an external programming device 52 by means of an appropriate communication link 54. The communication link 54 may be any suitable electromagnetic link such as an RF (radio frequency) channel.

Commands may be sent by the medical practitioner to the control system 30 from the external programmer 52 through the communication link 54. Similarly, through this communication link 54 and the external programmer 52, data (either held within the control system 30, as in a data latch, or stored within the memory circuit 44) may be transmitted by the pacemaker 10 to the external programmer 52. In this manner, noninvasive communication may be established with the implanted pacemaker 10 from a remote, non-implanted location.

The operation of the pacemaker 10 is generally controlled by a control program stored in the memory circuit 44 and executed by the control system 30. This control program usually consists of multiple integrated program modules, with each module bearing responsibility for controlling one or more functions of the pacemaker 10. For example, one program module may control the delivery of stimulating pulses to the heart 12, while another module may control the acquisition of atrial and ventricular electrical signals. In effect, each program module is a control program dedicated to a specific function or a set of functions of the pacemaker 10.

The enhanced 2:1 block response control program of the present invention, described below in connection with FIG. 5, operates on several rates measured in beats per minute (bpm) and intervals which are measured in milliseconds (ms). An interval in milliseconds is inversely proportional to the rate in beats per minute. The conversion between the interval and the corresponding rate is accomplished by dividing 60,000 by the interval to get the rate, or by dividing 60,000 by the rate to get the interval. For example, if the interval is 300 ms, the corresponding rate is 60,000÷300, or 200 bpm.

Before describing the control program in greater detail it would be helpful to define the terminology of the various rates and intervals used in the operation of the control program. It would also be helpful to describe the relationships between the various rates and intervals used in the operation of the control program.

An intrinsic atrial rate is determined by the control system 30 by first measuring the interval in milliseconds between the P-wave sensed during the current cardiac cycle and the P-wave sensed during the previous cardiac cycle, and then dividing 60,000 by the interval to produce the intrinsic atrial rate in beats per minute (bpm). A maximum tracking rate (MTR) is typically the maximum rate at which the pacemaker 10 (FIG. 1) tracks the atrial rate when pacing the ventricles. The MTR is programmable by the medical practitioner using the external programmer 52 (FIG. 1). A typical value for the MTR may be 160 bpm. A "base rate" is typically the minimum programmed pacing rate for a particular patient. If the intrinsic atrial rate drops below the base rate, the patient is paced at the base rate. The base rate is programmable by the medical practitioner using the external programmer 52 (FIG. 1). A typical value for the base rate may be 80 bpm.

A total atrial refractory period (TARP) is made up of two segments. The first segment, known as the AV delay (AVD), is initiated by a paced atrial event (such as an A-pulse) generated by the atrial pulse generator 22 (FIG. 1), or by a sensed atrial event (such as a P-wave) sensed by the atrial sense channel amplifier 26 (FIG. 1). The second segment, known as the post ventricular atrial refractory period (PVARP), is initiated by a paced ventricular event (such as a V-pulse) generated by the ventricular pulse generator 24 (FIG. 1), or by a sensed ventricular event (such as an R-wave) sensed by the ventricular sense channel amplifier 28 (FIG. 1). The TARP is the sum of the two segments (AVD and PVARP).

The block entry rate is the atrial rate at which the 2:1 block response mode is entered, while the block exit rate is the rate at which the 2:1 block response mode is exited. The block entry rate is inversely proportional to the TARP. For example if the TARP is 375 ms, the block entry rate is 60,000÷375) or 160 bpm. Similarly, the block exit rate is also inversely proportional to the TARP. Thus, the TARP determines the rate of entry into, and exit from, the 2:1 block response mode. Typically, the block entry rate is not equal to the MTR so that the 2:1 block response mode is entered when the intrinsic atrial rate exceeds the TARP. It should be noted that the block entry rate may be set to the same or a different value from the MTR without a departure from the spirit of this invention.

The TARP may be varied by adjusting one or both of its segments. The PVARP segment is commonly a constant value programmable by the medical practitioner using the external programmer 52 (FIG. 1). A typical value of the PVARP may be 275 ms. The AVD may be a constant programmable value, but is preferably shortened by the control system 30 (FIG. 1) when the intrinsic atrial rate increases, and lengthened by the control system 30 (FIG. 1) when the intrinsic atrial rate decreases. This adjustable AVD is called a rate-responsive AV delay (RRAVD).

Figures 2, 3:
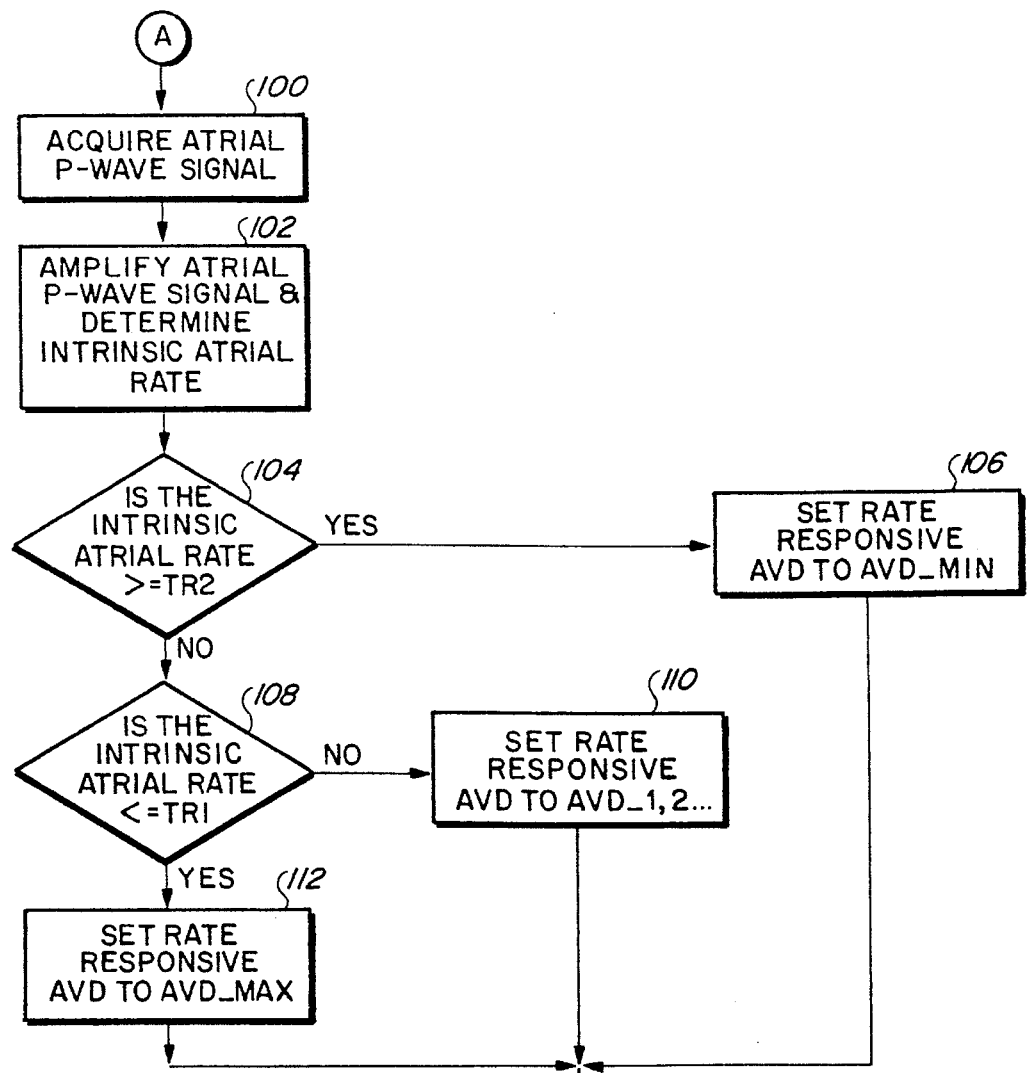
FIG. 2 is a table representing an example of AVD values and corresponding atrial rates for use with the pacemaker of FIG. 1.
FIG. 3 depicts a graph of the intrinsic atrial rate, the sensed functional atrial rate, and the RRAVD plotted over time, representing a standard 2:1 block response of a previously known pacemaker.
Figure 3:
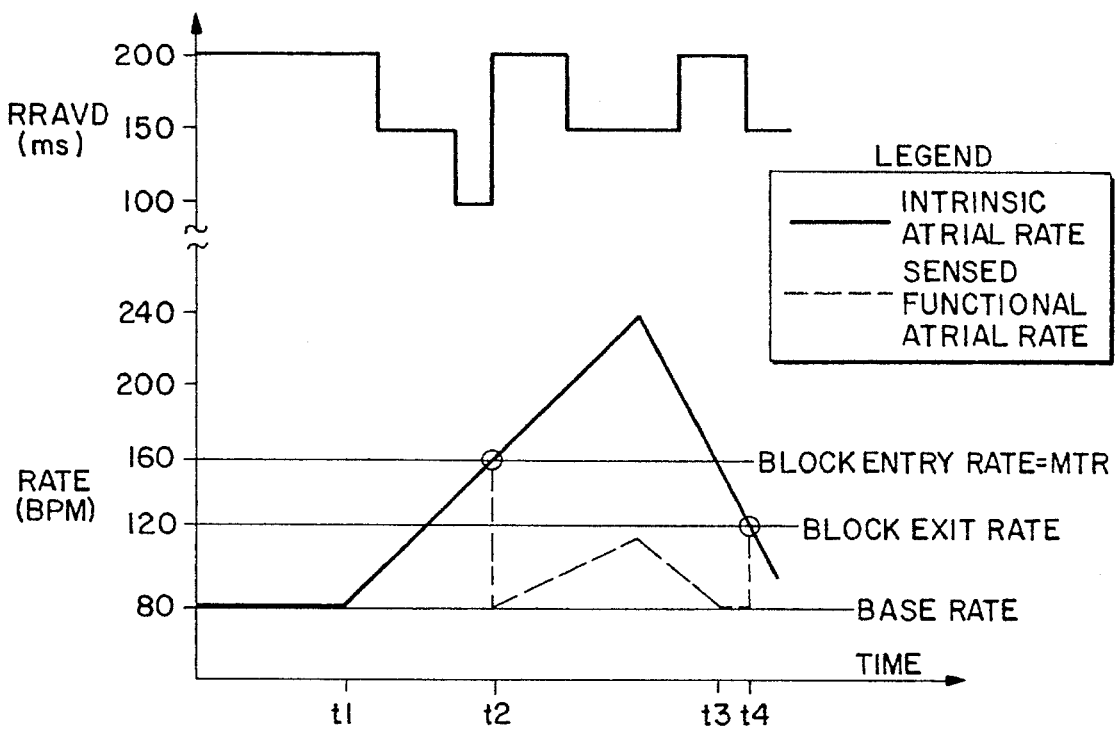

The RRAVD may be better understood by the example shown in FIG. 2. The RRAVD has a maximum value, AVD_max, which is generally maintained when the intrinsic atrial rate is less than or equal to a first threshold rate (TR1), and a minimum value, AVD_min, which is generally maintained when the intrinsic atrial rate is greater than or equal to a second threshold rate (TR2). Both TR1 and TR2 may be programmed by a medical practitioner. One or more intermediate RRAVD values (e.g. AVD_1, AVD_2, etc.) may be programmed as increments between AVD_max and AVD_min corresponding to changes in the intrinsic atrial rate between TR1 and TR2. In FIG. 2, one such incremental value, AVD_1, is shown corresponding to the atrial rate being between the TR1 and the TR2.

As shown in the example of FIG. 2, the AVD_min is 100 ms, the AVD_1 is 150 ms, the AVD_max is 200 ms, the TR1 is 100 bpm, the TR2 is 140 bpm, and the PVARP is 275 ms.

Since the TARP is inversely proportional to the intrinsic atrial rate (because the RRAVD changes inversely with respect to changes in the intrinsic atrial rate), the TARP decreases in value as the intrinsic atrial rate increases. For example, if the intrinsic atrial rate is at 126 bpm, the AVD would be set to AVD_1 (150 ms) because the intrinsic atrial rate of 126 is between the TR1 of 100 bpm and the TR2 of 140 bpm. With the PVARP set by the medical practitioner to 275 ms, the TARP would be 425 ms (PVARP of 275 ms+AVD_1 of 150 ms). If the intrinsic atrial rate then increased to the value of the MTR (160 bpm), which is greater than the TR1 (140 bpm), the AVD would be set to AVD_min (100 ms) and the TARP would decrease to 375 ms (PVARP of 275 ms+AVD_min of 100 ms). Thus, the RRAVD function enables the pacemaker 10 (FIG. 1) to mimic the physiological refractory periods of a healthy heart which change in response to the atrial rate.

When the intrinsic atrial rate exceeds the MTR (or the block entry rate if it is set to a different value from the MTR), the interval between P-waves of each successive cycle decreases while the TARP does not decrease below its minimum value dictated by AVD_min (a TARP value of 375 ms in the above example). For example, when the intrinsic atrial rate is 170 bpm the interval between the P-wave of the current cycle and the P-wave of the previous cycle is 353 ms, and thus the P-wave of the current cycle falls within the TARP of 375 ms. Thus, when the intrinsic atrial rate exceeds the MTR, one P-wave in every cycle falls into the TARP.

Since pacing the ventricle at a rate exceeding the MTR may be dangerous, the P-waves occurring during the TARP are not counted for the purpose of pacing the ventricle. Instead, only the P-waves occurring outside the TARP are counted to produce a sensed functional atrial rate. Returning to the above example, since every other P-wave falls into the TARP and is thus ignored, the sensed functional atrial rate is equal to one half of the intrinsic atrial rate. Thus, when the intrinsic atrial rate exceeds the 2:1 block rate, the control system 30 (FIG. 1) no longer tracks the intrinsic atrial rate in order to pace the ventricle but instead paces the ventricle at the sensed functional atrial rate, thus initiating a 2:1 block response mode, since the ventricular pacing rate is now one half of the intrinsic atrial rate.

The pacemaker 10 (FIG. 1) as described thus far operates similarly to previously known peacemakers, except that previously known pacemakers differ from the pacemaker 10 (FIG. 1) in that they do not base their rate-responsive functions (such as the RRAVD) on a rate derived from continually sensed P-waves, including P-waves which fall into the TARP. As a result, previously known pacemakers base their RRAVD on the sensed functional atrial rate, ignoring the intrinsic atrial rate when it exceeds the MTR. As described above, when the intrinsic atrial rate exceeds the MTR (or the block entry rate if it is set to a different value from the MTR), and every other P-wave falls into the TARP, the 2:1 block response mode is entered and the sensed functional atrial rate drops to one half value of the intrinsic atrial rate.

In FIG. 3, a graph depicting an example of the 2:1 block response of a previously known pacemaker is described. In this example, the PVARP is 275 ms, the AVD_min is 100 ms, the AVD_1 is 150 ms, the AVD_max is 200 ms, the TR1 is 100 bpm, the TR2 is 140 bpm, the base rate is 80 bpm, and the MTR is 160 bpm.

When the intrinsic atrial rate is below the base rate, the atria and ventricles are paced at the base rate (80 bpm). At t1, the intrinsic atrial rate begins to increase until t2, when the intrinsic atrial rate reaches the MTR of 160 bpm. When the intrinsic atrial rate is below TR1 of 100 bpm, the RRAVD is at the AVD_max of 200 ms. When the intrinsic atrial rate exceeds the TR1 of 100 bpm, then RRAVD is shortened to the AVD_1 of 150 ms. When the intrinsic atrial rate reaches the TR2 of 140 bpm, the RRAVD is shortened to the AVD_min of 100 ms. Thus, when the intrinsic atrial rate exceeds 140 bpm, the TARP is 375 ms (PVARP of 275 ms+AVD_min of 100 ms) and the corresponding block entry rate is 160 bpm (60,000÷375).

From t1 to t2 the intrinsic atrial rate and the sensed functional atrial rate have the same slope (i.e. are at a 1:1 ratio) since no P-waves fall into the TARP. When the intrinsic atrial rate exceeds the block entry rate at t2, the 2:1 block response mode is entered and the sensed functional atrial rate becomes one half the value of the intrinsic atrial rate, dropping to 80 bpm. Since in previously known pacemakers the RRAVD is based on the sensed functional atrial rate, the RRAVD is reset from AVD_min of 100 ms to AVD_max of 200 ms because the sensed functional atrial rate of 85 bpm is less than the TR1 of 100 bpm. Thus at t2, when the intrinsic atrial rate exceeds the block entry rate and the 2:1 block response mode is initiated, the TARP is set to a new, higher value of 475 ms (PVARP of 275 ms+AVD_max of 200 ms). From t2 to t4 the RRAVD changes in accordance with the sensed functional atrial rate, for example, dropping to AVD_1 of 150 ms when the sensed functional atrial rate exceeds 100 bpm.

The approach of previously known pacemakers is problematic, as discussed above, since in order for the pacemaker to exit from the 2:1 block condition all P-waves must fall outside of the new 475 ms TARP of each cardiac cycle (set at t2). The block exit rate corresponding to the new TARP is 60,000÷475, or 126 bpm. Thus, the pacemaker exits the 2:1 block condition when the intrinsic atrial rate drops below the block exit rate of 126 bpm (i.e. the interval between each successive P-wave exceeds 475 ms) at t4. As a result, during the period between t3 (when the intrinsic atrial rate drops below the block entry rate) and t4 (when the intrinsic atrial rate drops below the block exit rate), the pacemaker forces the heart to remain at the 2:1 block condition even though the intrinsic atrial rate is at a safe value below the MTR.

Thus, since the block entry rate of 160 bpm and the block exit rate of 126 bpm are not equal, the above approach provides inconsistent rates of entry into, and exit from, the 2:1 block response mode, and thus unnecessarily extends the duration of the 2:1 block response mode resulting in discomfort to the patient. A discrepancy in the rates of entry into and exit from 2:1 block is also inconsistent with the physiological behavior of a healthy heart and may cause additional discomfort to the patient.

The pacemaker 10 (FIG. 1) of the present invention solves the above problem first, by continually monitoring the intrinsic atrial rate by sensing all P-waves, even the P-waves occurring during the TARP, and second, by basing changes in the RRAVD on the intrinsic atrial rate instead of the sensed functional atrial rate when the intrinsic atrial rate exceeds the MTR. The sensed functional atrial rate is still used for pacing the ventricles at the reduced rate, but the RRAVD values are set based on the intrinsic atrial rate and not on the sensed functional atrial rate.

Figure 4:
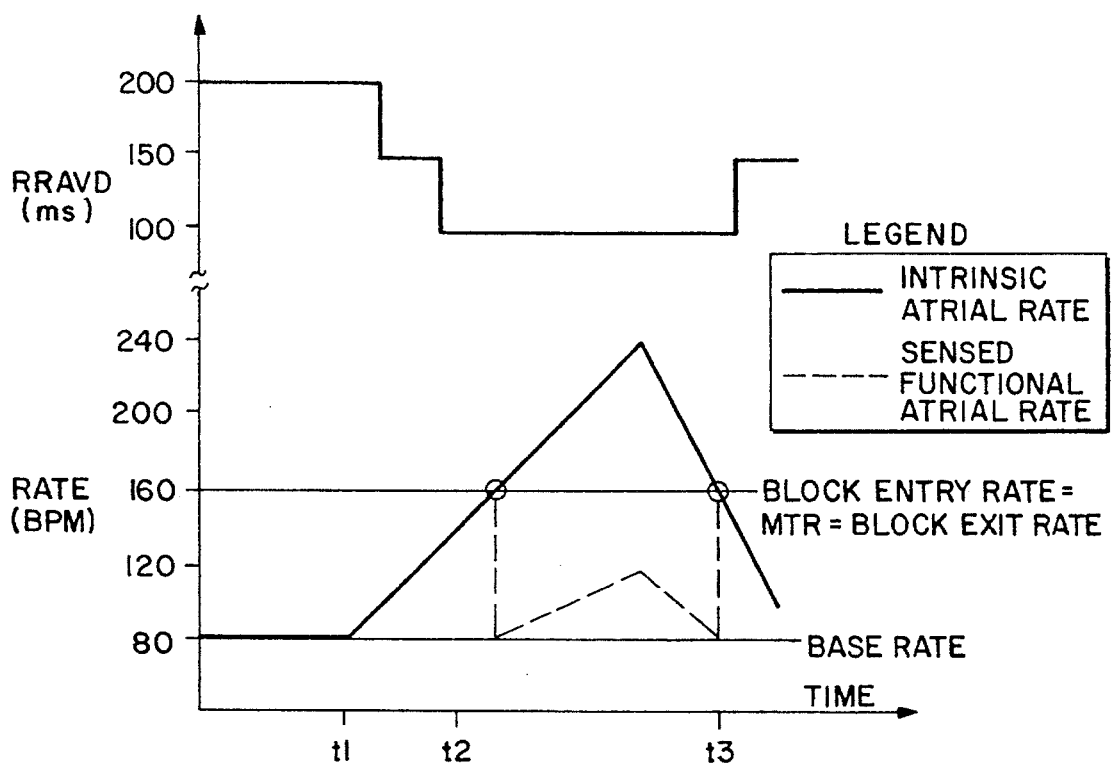
FIG. 4 depicts a graph of the intrinsic atrial rate, the sensed functional atrial rate, and the RRAVD plotted over time, representing a 2:1 block response of the pacemaker of FIG. 1 in accordance with the principles of the present invention.

As shown in FIG. 4, a graph depicting an example of the enhanced 2:1 block response of the pacemaker 10 (FIG. 1) of the present invention is described. In this example, the PVARP is 275 ms, the AVD_min is 100 ms, the AVD_1 is 150 ms, the AVD_max is 200 ms, the TR1 is 100 bpm, the TR2 is 140 bpm, the base rate is 80 bpm, and the MTR is 160 bpm. When the intrinsic atrial rate is below the base rate, the atria and ventricles are paced at the base rate (80 bpm). At t1, the intrinsic atrial rate begins to increase until t2 when the intrinsic atrial rate reaches the MTR of 150 bpm. The RRAVD is at the AVD_max of 200 ms until the intrinsic atrial rate reaches the TR1 of 100 bpm, when it is shortened to the AVD_1 of 150 ms. When the intrinsic atrial rate reaches the TR2 of 140 bpm, the RRAVD is shortened to the AVD_min of 100 ms. Thus, when the intrinsic atrial rate exceeds 140 bpm, the TARP is 375 ms (PVARP of 275 ms+AVD_min of 100 ms) and the corresponding block entry rate is 160 bpm (60,000÷375).

From t1 to t2 the intrinsic atrial rate and the sensed functional atrial rate have the same slope (i.e. are at a 1:1 ratio) since no P-waves fall into the TARP of each cardiac cycle. When the intrinsic atrial rate exceeds the block entry rate at t2, the 2:1 block response mode is entered and the sensed functional atrial rate becomes one half the value of the intrinsic atrial rate dropping to 80 bpm. In accordance with the principles of the present invention the RRAVD is based on the intrinsic atrial rate. Thus, the RRAVD continues to remain at AVD_min of 100 as long as the intrinsic atrial rate exceeds TR2 of 140 bpm. Thus at t2, when the intrinsic atrial rate exceeds the block entry rate and the 2:1 block response mode is initiated, the TARP remains at its value of 375 ms (PVARP of 275 ms+AVD_min of 100 ms). From t2 to t3 the RRAVD remains at AVD_min of 100 ms since the intrinsic atrial rate exceeds TR2 of 140 bpm.

The block exit rate corresponding to the TARP of 375 ms is 60,000÷375, or 160 bpm—equal to the block entry rate of 150 bpm. Thus, the pacemaker exits the 2:1 block response mode when the intrinsic atrial rate drops below the block exit rate of 160 bpm (i.e., the interval between successive P-waves exceeds 475 ms) at t3. As a result, the pacemaker 10 (FIG. 1) exits from the 2:1 block response mode as soon as the intrinsic atrial rate is at a safe level below the MTR (since MTR is equal to block exit rate). It should be noted that in practical applications there may be slight variations between the block entry rate and block exit rate which do not signify a departure from the spirit of this invention.

Thus, since the block entry rate and the block exit rate are equal, the pacemaker 10 (FIG. 1) of the present invention provides relatively consistent rates of entry into, and exit from, the 2:1 block response mode, minimizing patient discomfort accompanying the 2:1 block response mode and emulating the physiological behavior of a healthy heart. The pacemaker 10 (FIG. 1) of the present invention also remains in the 2:1 block response mode only as long as is necessary to respond to a high atrial rate exceeding the MTR.

As shown in FIG. 5, a logic flow diagram representing the control program for the control system 30 of FIG. 1 in accordance with the present invention is described. This control program is executed in a loop, continually providing the pacemaker 10 (FIG. 1) with the capability of entering into or exiting from a 2:1 block response mode at relatively consistent rates of entry and exit. Preferably, one complete loop of the control program follows a single cardiac cycle. After the control program begins at a step 100, the control system 30 (FIG. 1) allows the pacemaker 10 (FIG. 1) to acquire a P-wave signal from the atria (not shown) of the heart 12 (FIG. 1) through the electrode 18 (FIG. 1). At a step 102, the control system 30 (FIG. 1) causes the atrial amplifier 26 (FIG. 1) to amplify the P-wave signal, and then receives the amplified P-wave signal through the signal line 32 (FIG. 1). At the step 102, the control system 30 (FIG. 1) also determines the intrinsic atrial rate as described above.

At a test 104 the control system 30 (FIG. 1) determines if the intrinsic atrial rate is greater than or equal to the TR2. If the intrinsic atrial rate is greater than or equal to the TR2, the rate responsive AVD is set to its minimum value AVD_min at a step 106 and the 2:1 block response mode is entered. This step also results in the TARP being set to and kept at its minimum value (PVARP+AVD_min). As a result, the block entry rate and the block exit rate are equal to one another, since the TARP remains at its minimum value during the time the intrinsic atrial rate exceeds the MTR (and the block entry rate), as discussed above in connection with FIG. 4. The control system 30 (FIG. 1) then completes the loop by returning to the step 100 for the next cardiac cycle.

If, at the test 104, the control system 30 (FIG. 1) determines that the intrinsic atrial rate is less than the TR2, the control system 30 (FIG. 1) proceeds to a test 108. At the test 108, the control system 30 (FIG. 1) determines if the intrinsic atrial rate is less than or equal to the TR1. If the intrinsic atrial rate is not less than or equal to the TR1, at a step 110, the control system 30 (FIG. 1) sets rate responsive AVD equal to an incremental value between AVD_max and AVD_min. The exact value or values may be programmed by the medical practitioner using the external programmer 52 (FIG. 1). If at the test 108 the intrinsic atrial rate is less than or equal to the TR1, the rate responsive AVD is set to its maximum value of AVD_max at a step 112. The control system 30 (FIG. 1) then completes the loop by returning to the step 100 for the next cardiac cycle.

Thus, an implantable dual-chamber pacemaker programmed to operate primarily in an atrial tracking mode is provided, where the pacemaker continually monitors the intrinsic atrial rate including atrial events occurring during refractory periods and where the pacemaker maintains a consistent atrial rate of entry into, and exit from, a 2:1 block response mode by setting rate-responsive AV delay values in accordance with the continually monitored intrinsic atrial rate.

One skilled in the art will appreciate that the present invention can be practiced by other than the described embodiments, which are presented for purposes of illustration and not of limitation, and the present invention is limited only by the claims that follow.

What is claimed is:

1. An implantable pacemaker, comprising:

atrial sensing means for sensing an intrinsic atrial rate in an atrial chamber of the heart;

pulse generating means for generating pacing pulses for delivery to the atrial and ventricular chambers of the heart;

defining means for defining a block entry rate and a block exit rate, the block entry and block exit rates being substantially equal; and control means, coupled to the atrial sensing means, the pulse generating means, and to the defining means, for determining when the intrinsic atrial rate exceeds the block entry rate and when the intrinsic atrial rate falls below the block exit rate, and for pacing in the ventricle in a 2:1 block response when the intrinsic atrial rate exceeds the block entry rate and for terminating the 2:1 block response mode when the intrinsic atrial rate falls below the block exit rate.

2. The pacemaker of claim 1, further comprising:

means for defining a first threshold rate and a second threshold rate, wherein the pulse generating means generates pacing pulses for delivery to the ventricle at a rate not less than the first threshold rate and not greater than the second threshold rate.

3. The pacemaker of claim 2, further comprising:

means for defining a first atrial refractory period and a second atrial refractory period;

means for sensing at least one cardiac cycle;

means for defining a programmable total refractory period, comprising a sum of the first refractory period and the second refractory period, in each sensed cardiac cycle;

means for determining the intrinsic atrial rate by causing the atrial sensing means to sense all atrial events of each cardiac cycle, including atrial events occurring during the total refractory period of each cardiac cycle;

means for setting the second refractory period to a minimum value, corresponding to a minimum total refractory period, when the intrinsic atrial rate is greater than or equal to a second threshold rate; and means for defining the block entry rate and the block exit rate as being inversely proportional to the minimum total refractory period.

4. The pacemaker of claim 2, further comprising:

means for defining a first atrial refractory period and a second atrial refractory period;

means for sensing at least one cardiac cycle;

means for defining a programmable total refractory period, comprising a sum of the first refractory period and the second refractory period, in each sensed cardiac cycle;

means for determining the intrinsic atrial rate by causing the atrial sensing means to sense all atrial events of each cardiac cycle, including atrial events occurring during the total refractory period of each cardiac cycle;

means for setting the second refractory period to a maximum value, corresponding to a maximum total refractory period, when the intrinsic atrial rate is less than or equal to the first threshold rate;

means for setting the second refractory period to a minimum value, corresponding to a minimum total refractory period, when the intrinsic atrial rate is greater than or equal to a second threshold rate;

means for setting the second refractory period to at least one intermediate value, corresponding to at least one intermediate total refractory period, when the intrinsic atrial rate is greater than the first threshold rate and less than the second threshold rate;

means for determining a sensed functional atrial rate by counting atrial events which occur outside of the total refractory period of each cardiac cycle; and means for causing the pulse generating means to generate pacing pulses in the ventricular chamber at a ventricular pacing rate equal to the sensed functional atrial rate of each cardiac cycle.

5. The pacemaker of claim 4, wherein the control means comprises:

means for initiating a 2:1 block response mode, at which the sensed functional atrial rate is one half of the intrinsic atrial rate, when at least one atrial event occurs during the minimum total refractory period; and means for terminating the 2:1 block response mode when no atrial events occur during the minimum total refractory period.

6. An implantable pacemaker, comprising:

atrial sensing means for sensing an intrinsic atrial rate in the atrial chamber of the heart;

pulse generating means for generating pacing pulses for delivery to the atrial and ventricular chambers;

defining means for defining a base rate and a maximum tracking rate (MTR); and control means, coupled to the atrial sensing means, the pulse generating means, and to the defining means, for pacing the ventricular chamber so that the ventricular chamber is paced at a rate at least equal to the base rate, and at most equal to the MTR, the control means further comprising:

means for defining a programmable post ventricular atrial refractory period (PVARP);

means for defining a rate responsive AV delay (RRAVD);

means for sensing at least one cardiac cycle;

means for defining a programmable total atrial refractory period (TARP) comprising a sum of the PVARP and the RRAVD in each sensed cardiac cycle;

means for determining the intrinsic atrial rate by causing the atrial sensing means to sense all atrial events of each cardiac cycle, including atrial events occurring during the TARP of each cardiac cycle;

means for setting the RRAVD to a maximum value, corresponding to a maximum TARP, when the intrinsic atrial rate is less than or equal to the base rate;

means for setting the RRAVD to a minimum value, corresponding to a minimum TARP, when the intrinsic atrial rate is greater than or equal to a second threshold rate; and means for setting the RRAVD to at least one intermediate value, corresponding to an intermediate TARP, when the intrinsic atrial rate is greater than the base rate and less than the second threshold rate.

7. The pacemaker of claim 6, further comprising defining means for defining a block entry rate at which a 2:1 block response mode is initiated, the block entry rate being inversely proportional to the minimum TARP, and a block exit rate at which the 2:1 block response mode is terminated, the block exit rate being inversely proportional to the minimum TARP.

8. The pacemaker of claim 6, wherein the control means comprises:

means for determining a sensed functional atrial rate by counting atrial events which occur outside of the TARP of each cardiac cycle; and means for causing the pulse generating means to generate pacing pulses in the ventricular chamber at a ventricular pacing rate equal to the sensed functional atrial rate of each cardiac cycle.

9. The pacemaker of claim 8, wherein the control means comprises:

means for initiating a 2:1 block response mode, during which the sensed functional atrial rate is one half of the intrinsic atrial rate, when at least one atrial event occurs during the minimum TARP; and means for terminating the 2:1 block response mode when no atrial events occur during the minimum TARP.

10. An implantable pacemaker, comprising:

means for defining a programmable total refractory period;

atrial sensing means for sensing an intrinsic atrial rate in an atrial chamber of a heart, the atrial sensing means comprising means for sensing atrial events during the total refractory period;

pulse generating means for generating pacing pulses for delivery to the atrial and ventricular chambers;

means for defining a block entry rate and a block exit rate, the block entry and block exit rates being substantially equal; and first trigger means for initiating a 2:1 block response when the intrinsic atrial rate exceeds the block entry rate; and second trigger means for terminating a 2:1 block response when the intrinsic atrial rate decreases below the block exit rate.

11. The pacemaker of claim 10, wherein the means for defining a programmable total refractory period includes means for defining first and second refractory periods which are programmable by the physician, and for defining the total refractory period as the sum of the first and the second refractory periods, the pacemaker further comprising:

means for defining a first threshold rate and a second threshold rate, wherein the pulse generating means generates pacing pulses for delivery to the ventricle at a rate at least equal to the first threshold rate, and at most equal to the second threshold rate;

monitoring means for determining when the intrinsic atrial rate is less than or equal to the first threshold rate, for determining when the intrinsic atrial rate is greater than or equal to the second threshold rate, and for determining when the intrinsic atrial rate is greater than the first threshold rate and less than the second threshold rate; and selection means, responsive to the monitoring means, for automatically setting the second refractory period to a maximum value when the intrinsic atrial rate is less than or equal to a first threshold rate, for automatically setting the second refractory period to a minimum value when the intrinsic atrial rate is greater than or equal to a second threshold rate, and for automatically setting the second refractory period to at least one intermediate value when the intrinsic atrial rate is greater than the first threshold rate and less than the second threshold rate, whereby:

when the second refractory period is set to a minimum value, the total refractory period is equal to a minimum total refractory period;

when the second refractory period is set to at least one intermediate value, the total refractory period is equal to at least one intermediate total refractory period; and when the second refractory period is set to a maximum value, the total refractory period is equal to a maximum total refractory period.

12. The pacemaker of claim 11 further comprising means for defining the block entry rate and the block exit rate as being inversely proportional to the minimum total refractory period.

13. The pacemaker of claim 11, further comprising:

means for determining a sensed functional atrial rate by counting atrial events which occur outside of the total refractory period of each cardiac cycle; and third trigger means for causing the pulse generating means to generate pacing pulses in the ventricular chamber at a ventricular pacing rate equal to the sensed functional atrial rate of each cardiac cycle.

14. The pacemaker of claim 13, further comprising:

means for initiating a 2:1 block response mode, at which the sensed functional atrial rate is one half of the intrinsic atrial rate, when at least one atrial event occurs during the minimum total refractory period; and means for terminating a 2:1 block response mode, at which the sensed functional atrial rate is one half of the intrinsic atrial rate, when no atrial events occur during the minimum total refractory period.

15. a method of operating an implantable pacemaker comprising the steps of:

coupling the pacemaker to, respectively, an atrial chamber and a ventricular chamber of a heart;

generating pacing pulses for delivery to the atrial and ventricular chambers of the heart;

defining a first refractory period and a second refractory period which are programmable by the physician;

defining a programmable total refractory period comprising a sum of the first refractory period and the second refractory period;

sensing an intrinsic atrial rate in an atrial chamber of the heart, including sensing of atrial events during the total refractory period;

defining a first threshold rate and a second threshold rate;

determining when the intrinsic atrial rate is less than or equal to the first threshold rate, when the intrinsic atrial rate is greater than or equal to the second threshold rate, and when the intrinsic atrial rate is greater than the first threshold rate and less than the second threshold rate; and automatically selecting a maximum value for the second refractory period when the intrinsic atrial rate is less than or equal to a first threshold rate, automatically selecting a minimum value for the second refractory period when the intrinsic atrial rate is greater than or equal to a second threshold rate, and automatically selecting at least one intermediate value for the second refractory period when the intrinsic atrial rate is greater than the first threshold rate and less than the second threshold rate;

whereby the total refractory period equals a minimum total refractory period when the second refractory period is set to a minimum value, the total refractory period equals at least one intermediate total refractory period when the second refractory period is set to at least one intermediate value, and the total refractory period equals a maximum total refractory period when the second refractory period is set to a maximum value.

16. The method of claim 15, further comprising the steps of:

defining a block entry rate at which a 2:1 block response mode is entered, as being inversely proportional to the minimum total refractory period; and defining a block exit rate at which the 2:1 block response mode is exited, as being inversely proportional to the minimum total refractory period, wherein the block entry and exit rates are substantially equal.

17. The method of claim 15, further comprising the steps of:

determining a sensed functional atrial rate by only counting atrial events which occur outside of the total refractory period of each cardiac cycle; and generating pacing pulses in the ventricular chamber at a ventricular pacing rate equal to the sensed functional atrial rate of each cardiac cycle.

18. The method of claim 17, further comprising the steps of:

initiating a 2:1 block response mode, at which the sensed functional atrial rate is one half of the intrinsic atrial rate, when at least one atrial event occurs during the minimum total refractory period; and terminating a 2:1 block response mode, at which the sensed functional atrial rate is one half of the intrinsic atrial rate, when no atrial events occur during the minimum total refractory period.

* * * * *